(12) United States Patent
Jiang et al.

(10) Patent No.: US 6,686,349 B2
(45) Date of Patent: Feb. 3, 2004

(54) SUBSTITUTED TETRACYCLIC PYRROLOQUINOLONE DERIVATIVES USEFUL AS PHOSPHODIESTERASE INHIBITORS

(75) Inventors: Weiqin Jiang, Bridgewater, NJ (US); Zhihua Sui, Flemington, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/291,978

(22) Filed: Nov. 12, 2002

(65) Prior Publication Data

US 2003/0144268 A1 Jul. 31, 2003

Related U.S. Application Data

(60) Provisional application No. 60/332,977, filed on Nov. 14, 2001.

(51) Int. Cl.$^7$ ............... C07D 471/14; C07D 498/14; A61K 31/4985; A61K 31/551
(52) U.S. Cl. ............... 514/211.04; 514/218; 514/229.5; 514/255.02; 540/488; 540/498; 544/99; 544/343
(58) Field of Search ............... 514/211.04, 218, 514/229.5, 255.02; 540/488, 498; 544/99, 343

(56) References Cited

U.S. PATENT DOCUMENTS

| 4,235,907 | A  | 11/1980 | Pfenninger ............ 424/258 |
| 5,859,009 | A  | 1/1999  | Schaper et al. ......... 514/229.2 |
| 6,143,746 | A  | 11/2000 | Daugan et al. ......... 514/249 |
| 6,492,358 | B2 | 12/2002 | Sui et al. ............. 514/232.8 |

FOREIGN PATENT DOCUMENTS

| EP | 0740668 B1    | 7/1998  |
| WO | WO 95/19978 A1 | 7/1995  |
| WO | WO 97/03675 A1 | 2/1997  |
| WO | WO 01/87882 A2 | 11/2001 |

OTHER PUBLICATIONS

Carniaux, et al., "Synthesis of a Novel Fused Tricyclic Quinolone system via Oxidation of 1,2,3,4–Tetrahydro–β–Carbolines." Tetrahedron Letters (1997), 38(17), 2997–3000.

Nakagawa, et al., "Synthetic Approaches to Fumitremorgins.III. Synthesis of Optically Active Pentacyclic Ring Systems, and Their Oxidation at Ring C[1])" Chem. Pharm. Bull. (1989), 37(1), 23–32.

Wang, et al., "A Biomimetic Total Synthesis of (–)–Spirotryprostatin B and Related Studies" J. Org. Chem. (2000), 65, 4685–4693.

Wang, et al., "Synthesis and Evaluation of Tryprostatin B and Demethoxyfumitremorgin C Analogues" J. Med. Chem. (2000), 43, 1577–1585.

Wang, et al., "The N–Acyliminium Pictet–Spengler Condensation as a Multicomponent Combinatorial Reaction on Solid Phase and Its Application to the Synthesis of Demethoxyfumitremorgin C Analogues" Organic Letters (1999), 1(10), 1647–1649.

*Primary Examiner*—Bruck Kifle

(57) ABSTRACT

The invention relates to novel tetracyclic pyrroloquinolone derivatives of the formula (I) or (II):

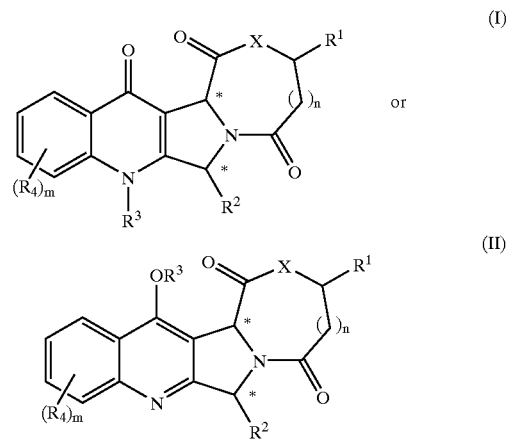

wherein all variables are as herein defined, pharmaceutical compositions containing the compounds and their use for the treatment of sexual dysfunction.

12 Claims, No Drawings

SUBSTITUTED TETRACYCLIC PYRROLOQUINOLONE DERIVATIVES USEFUL AS PHOSPHODIESTERASE INHIBITORS

CROSS REFERENCE TO RELATED APPLICATION

This application claims the benefit of U.S. Provisional Application No. 60/332,977, filed on Nov. 14, 2001, which is incorporated by reference herein in its entirety.

FIELD OF THE INVENTION

The invention relates to novel tetracyclic pyrroloquinolone derivatives, intermediates used in, synthesis of and pharmaceutical compositions containing the compounds and their use for the treatment of sexual dysfunction. The compounds of the present invention are phosphodiesterase inhibitors useful for the treatment of sexual dysfunction, more particularly male erectile dysfunction.

BACKGROUND OF THE INVENTION

Erectile dysfunction (ED) is defined as the inability to achieve or maintain an erection sufficiently rigid for satisfactory sexual intercourse. Currently it is estimated that approximately 7–8% of the male population suffer from some degree of ED, the equivalent of at least 20 million men in the United States alone. Since the likelihood of ED increases with age, it is projected that the incidence of this condition will rise in the future as the average age of the population increases.

Male erectile dysfunction may be the consequence of psychogenic and/or organic factors. Although ED is multifactorial, certain sub-groups within the male population are more likely to present with the symptoms of the disorder. In particular, patients with diabetes, hypertension, heart disease, and multiple sclerosis have a particularly high prevalence of ED. In addition, patients who take certain classes of drugs such as antihypertensives, antidepressants, sedatives, and anxiolytics are more prone to suffer from ED.

Treatments for ED include a variety of pharmacologic agents, vacuum devices, and penile prostheses. Among the pharmacologic agents, papaverine, phentolamine, and alprostadil are currently used in practice. These agents are only effective after direct intracavernosal or intraurethral injection, and are associated with side effects such as priapism, fibrosis, penile pain and hematoma at the injection site. Vacuum devices are a noninasive alternative treatment for ED. These devices produce an erection by creating a negative pressure around the shaft of the penis resulting in an increased blood flow into the corpus cavernosum via passive arterial dilation. Although this form of therapy is frequently successful in ED of organic origin, complaints include the lack of spontaneity and the time involved in using a mechanical device, and difficulty and discomfort with ejaculation. A variety of semi-rigid or inflatable penile prostheses have been used with some success, particularly in diabetic men. These devices are generally considered when other treatment options have failed, and are associated with an increased risk of infection and ischemia.

Recently, the phosphodiesterase V (PDEV) inhibitor, sildenafil (Viagra®) was approved by the FDA as an orally effective medication for the treatment of ED. Sildenafil, 5-[2-ethoxy-5-(4-methylpiperazin-1-ylsulphonyl)phenyl]-1-methyl-3-n-propyl-6,7-dihydro-1H-pyrazolo[4,3-d]pyrimidin-7-one and a number of related analogs and their use as antianginal agents are described in U.S. Pat. Nos. 5,250,534 and 5,346,901. The use of sildenafil and related analogs for treating male erectile dysfunction is described in PCT International Application Publication No. WO 94/28902, published Dec. 22, 1994. In clinical studies, the drug improved sexual function in about 70% of the men who suffer from ED of psychogenic or organic etiology. However, the drug showed less dramatic efficacy in patients who had undergone a radical prostatectomy, with improved erections in 43% of patients who took sildenafil versus 15% on placebo. In addition, the use of sildenafil is associated with several undesirable side effects including headache, flushing and disrupted color vision which result from nonselective effects on a variety of tissues. In spite of these shortcomings, the drug is viewed by patients as preferable to other treatments which involve the introduction of medication directly into the penis via injection, the use of an external device or a surgical procedure.

Daugan et.al, in WO 95/19978, U.S. Pat. No. 5,859,009, U.S. Pat. No. 6,143,746 and EP 0740668 B1 describe the synthesis of a series of tetracyclic derivatives as inhibitors of cyclic guanosine 3',5' monophosphate specifically phosphodiesterase, and their use in treating cardiovascular disorders. Daugan et.al., in WO97/03675 teach the use of the tetracyclic derivatives for the treatment of impotence.

Garinaux, J.-F. et al., in *Tetrahedron Letters* 38(17), (1997), pp 2997–3000 disclose the synthesis of tricyclic quinolone derivatives via oxidation of 1,2,3,4-tetrahydro-β-carbolines.

Pfenninger, E. in DE 2803541 and U.S. Pat. No. 4,235,907 discloses substituted 9H-pyrrolo-[3,4-b]quinolin-9-ones and their use in the treatment of allergic asthma.

Sexually stimulated penile erection results from a complex interplay of physiological processes involving the central nervous system, the peripheral nervous system, and the smooth muscle. Specifically, release of nitric oxide from the non-adrenergic, non-cholinergic nerves and endothelium activates guanylyl cyclase and increases intracellular cGMP levels within the corpus cavernosum. The increase in intracellular cGMP reduces intracellular calcium levels, resulting in trabecular smooth muscle relaxation, which, in turn, results in corporal volume expansion and compression of the sub-tunical venules leading to penile erection.

PDEV has been found in human platelets and vascular smooth muscle, suggesting a role for this enzyme in the regulation of intracellular concentrations of cGMP in cardiovascular tissue. In fact, inhibitors of PDEV have been shown to produce endothelial-dependent vasorelaxation by potentiating the increases in intracellular cGMP induced by nitric oxide. Moreover, PDEV inhibitors selectively lower the pulmonary arterial pressure in animal models of congestive heart failure and pulmonary hypertension. Hence in addition to their utility in ED, PDEV inhibitors would likely be of therapeutic benefit in conditions like heart failure, pulmonary hypertension, and angina.

Agents that increase the concentration of cGMP in penile tissue, either through enhanced release or reduced breakdown of cGMP, are expected to be effective treatments for ED. The intracellular levels of cGMP are regulated by the enzymes involved in its formation and degradation, namely the guanylate cyclases and the cyclic nucleotide phosphodiesterases (PDEs). To date, at least nine families of mammalian PDEs have been described, five of which are capable of hydrolyzing the active, cGMP, to the inactive, GMP, under physiological conditions (PDEs I, II, V, VI, and IX). PDE V is the predominant isoform in human corpus cavernosum.

Inhibitors of PDEV, therefore, would be expected to increase the concentration of cGMP in the corpus cavernosum and enhance the duration and frequency of penile erection.

Additionally, selective PDE inhibitors are known to be useful in the treatment of various disorders and conditions including male erectile dysfunction (ED), female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications.

Accordingly, it is an object of the invention to identify compounds which increase the concentration of cGMP in penile tissue through the inhibition of phosphodiesterases, specifically PDEV. It is another object of the invention to identify compounds which are useful for the treatment of sexual dysfunction, particularly erectile dysfunction and/or impotence in male animals and sexual dysfunction in female animals. Still another object of the invention is to identify methods for treating sexual dysfunction, especially erectile dysfunction, using the compounds of the present invention.

It is another object of the invention to identify compounds which are useful for the treatment of conditions of disorders mediated by PDEV, such as male erectile dysfunction, female sexual dysfunction, cardiovascular disorders, atherosclerosis, arterial occlusive disorders, thrombosis, coronary reststenosis, angina pectoris, myocardial infarction, heart failure, ischemic heart disorders, hypertension, pulmonary hypertension, asthma, intermittent claudication or diabetic complications.

We now describe a series of tetracyclic pyrroloquinolone derivatives with the ability to inhibit phosphodiesterase type V (PDEV) in enzyme assays.

SUMMARY OF THE INVENTION

The present invention provides novel tetracyclic pyrroloquinolone derivative compounds useful as phosphodiesterase inhibitors. More particularly, the present invention is directed to compounds of the general formula (I) or (II):

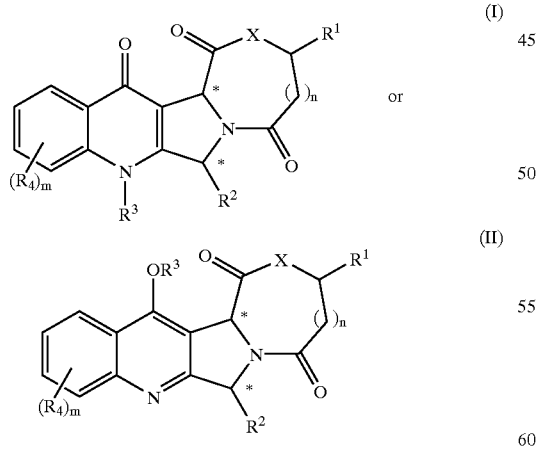

wherein

X is selected from the group consisting of O and $NR^6$;

$R^6$ is selected from the group consisting of hydrogen, $C_{1-6}$alkyl, $C_{2-6}$alkenyl, $C_{2-6}$alkynyl, halo$C_{1-6}$alkyl, $C_{3-8}$cycloalkyl, $C_{3-8}$cycloalkyl$C_{1-3}$alkyl, aryl$C_{1-3}$alkyl and heteroaryl$C_{1-3}$alkyl;

wherein the aryl part of the aryl$C_{1-3}$alkyl group is phenyl or phenyl substituted with one or more substituents selected from halogen, $C_{1-6}$alkyl, $C_{1-6}$alkoxy and methylenedioxy; wherein the heteroaryl part of the heteroaryl$C_{1-3}$alkyl group is selected from thienyl, furyl or pyridyl wherein the thienyl, furyl or pyridyl group is optionally substituted with one or more substituents independently selected from halogen, $C_{1-6}$akyl or $C_{1-6}$alkoxy;

$R^1$ is selected from the group consisting of hydrogen and $C_{1-3}$alkyl;

Alternatively when X is $NR^6$, $R^6$ and $R^1$ may be taken together as $C_{3-4}$alkyl or $C_{3-4}$alkenyl;

n is an integer from 0 to 1;

$R^2$ is selected from the group consisting of $C_5$–$C_{10}$alkyl (optionally substituted with one to three substituents independently selected from halogen, hydroxy, nitro, amino, $NHR^A$ or $N(R^A)_2$), aryl (optionally substituted with one to three substituents independently selected from $R^C$), cycloalkyl (optionally substituted with one to three substituents independently selected from $R^A$), heteroaryl (optionally substituted with one to three substituents independently selected from $R^C$), and heterocycloalkyl (optionally substituted with one to three substituents independently selected from $R^C$);

where each $R^A$ is independently selected from the group consisting of $C_1$–$C_6$alkyl, aryl, $C_1$–$C_6$aralkyl and heteroaryl, where the aryl, aralkyl or heteroaryl may be optionally substituted with one to three $R^B$;

where each $R^B$ is independently selected from the group consisting of halogen, nitro, cyano, $C_1$–$C_6$alkyl, $C_1$–$C_6$alkoxy, $C_1$–$C_6$alkylcarbonyl, carboxy$C_1$–$C_6$alkyl, $C_1$–$C_6$alkylsulfonyl, trifluoromethyl, amino, di($C_1$–$C_6$alkyl) amino, acetylamino, carboxy$C_1$–$C_6$alkylcarbonylamino, hydroxy$C_1$–$C_6$alkylamino, $NHR^A$ and $N(R^A)_2$;

where $R^C$ is selected from the group consisting of halogen, hydroxy, nitro, cyano, —$CO_2R^D$, $C_1$–$C_6$alkyl, $C_1$–$C_6$alkoxy, trifluoromethyl, trifluoromethoxy, $NR^DR^E$ and aryl$C_{1-3}$alkyl;

where $R^D$ is selected from the group consisting of hydrogen and $C_{1-6}$alkyl; and where $R^E$ is selected from the group consisting of hydrogen, $C_{1-6}$alkyl, $C_{2-7}$alkylcarbonyl and $C_{1-6}$alkylsulfonyl;

$R^3$ is selected from the group consisting of hydrogen, $C_{1-6}$alkyl, $C_1$–$C_6$alkylcarbonyl, $C_2$–$C_6$alkenylcarbonyl and $C_2$–$C_6$alkynylcarbonyl;

m is and integer from 0 to 4;

$R^4$ is independently selected from the group consisting of halogen, nitro, hydroxy, $C_1$–$C_6$alkyl, $C_1$–$C_6$alkoxy, —$NH_2$, —$NHR^A$, —$N(R^A)_2$, —$OR^A$, —$C(O)NH_2$, —$C(O)NHR^A$, —$C(O)N(R^A)_2$, —$NHC(O)R^A$, —$SO_2NHR^A$, —$SO_2N(R^A)_2$, where $R^A$ is as defined above, phenyl (optionally substituted with one to three substituents independently selected from $R^B$), heteroaryl (optionally substituted with one to three substituents independently selected from $R^B$) and heterocycloalkyl (optionally substituted with one to three substituents independently selected from $R^B$);

and pharmaceutically acceptable salts thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention is a method of treating a condition selected from the group consisting of male erectile dysfunction (ED), impotence, female sexual dysfunction, female sexual arousal dysfunction, female sexual dysfunction related to blood flow and nitric oxide production in the tissues of the vagina and clitoris, premature labor, dysmenorrhea, cardiovascular disorders, atherosclerosis, arterial occlusive disorders, thrombosis, coronary rest stenosis, angina pectoris, myocardial infarction, heart failure, ischemic heart disorders, hypertension, pulmonary hypertension, asthma, intermittent claudication and diabetic complications in a subject in need thereof comprising administering to the subject a therapeutically effective amount of any of the compounds or pharmaceutical compositions described above.

An example of the invention is a method for increasing the concentration of cGMP in penile tissue through the inhibition of phosphodiesterases, specifically PDEV, in a male subject in need thereof comprising administering to the subject an effective amount of any of the compounds or pharmaceutical compositions described above.

Further exemplifying the invention is a method of producing endothelial-dependent vasorelaxation by potentiating the increases in intracellular cGMP induced by nitric oxide in a subject in need thereof comprising administering to the subject an effective amount of any of the compounds or pharmaceutical compositions described above.

Another example of the invention is the use of any of the compounds described above in the preparation of a medicament for: (a) treating sexual dysfunction, especially male erectile dysfunction, (b) treating impotence, (c) increasing the concentration of cGMP in penile tissue through inhibition of phosphodiesterase, especially PDEV and/or (d) treating a condition selected from the group consisting of premature labor, dysmenorrhea, cardiovascular disorders, atherosclerosis, arterial occlusive disorders, thrombosis, coronary reststenosis, angina pectoris, myocardial infarction, heart failure, ischemic heart disorders, hypertension, pulmonary hypertension, asthma, intermittent claudication and diabetic complications in a subject in need thereof.

DETAILED DESCRIPTION OF THE INVENTION

The present invention provides novel tetracyclic pyrroloquinolone derivatives useful for the treatment of sexual dysfunction, particularly male erectile dysfunction (ED). Although the compounds of the present invention are useful primarily for the treatment of male sexual dysfunction or erectile dysfunction, they may also be useful for the treatment of female sexual dysfunction, for example female sexual arousal dysfunction, female sexual dysfunction related to blood flow and nitric oxide production in the tissue of the vagina and clitoris, and of premature labor and dysmenorrhea.

More particularly, the compounds of the present invention are of the formula (I) or (II):

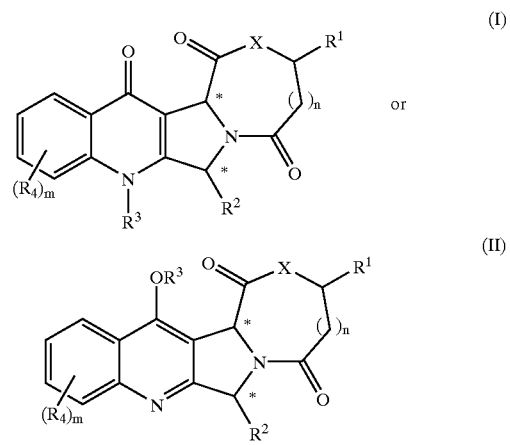

wherein X, $R^1$, n, $R^2$, $R^3$, m, $R^4$ and $R^5$ are as defined above, and pharmaceutically acceptable salts thereof.

In an embodiment of the present invention X is $NR^6$. In another embodiment of the present invention $R^6$ is selected from the group consisting of hydrogen and lower alkyl. In yet another embodiment of the present invention, $R^6$ is selected from the group consisting of hydrogen, $C_{1-4}$alkyl, aryl$C_{1-3}$alkyl and heteroaryl$C_{1-3}$alkyl, preferably $R^6$ is selected from the group consisting of hydrogen, methyl, benzyl and 2-pyridyl methyl, more preferably $R^6$ is selected from the group consisting of methyl and 2-pyridyl methyl.

In an embodiment of the present invention $R^1$ is selected from the group consisting of hydrogen and methyl. In an embodiment of the present invention, X is $NR^6$ and $R^1$ and $R^6$ are taken together as $C_{3-4}$alkyl or $C_{3-4}$alkenyl.

In an embodiment of the present invention n is an integer from 0 to 2. Preferably n is an integer from 0 to 1, more preferably n is 0.

In an embodiment of the present invention $R^2$ is a monocyclic ring structure selected from phenyl, thienyl, furyl or pyridyl; or a bicyclic ring system of the general formula

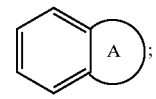

wherein the bicyclic ring structure is attached to the rest of the molecule via one of the benzene carbon atoms; wherein the fused ring A is a 5- or 6-membered saturated, partially unsaturated or fully unsaturated ring structure and which comprises carbon atom and optionally one to two heteroatoms selected from the group consisting of O, S and N;

wherein the benzene portion of the ring structure is optionally substituted with one or more substituents independently selected from halogen, hydroxy, $C_{1-6}$alkyl, $C_{1-6}$alkoxy, —$CO_2R^B$, halo$C_{1-6}$alkyl, halo$C_{1-6}$alkoxy, cyano, nitro or $NR^AR^B$; where $R^A$ is selected from the group consisting of hydrogen, $C_{1-6}$alkyl, $C_{2-7}$alkylcarbonyl and $C_{1-6}$alkylsulfonyl; and where $R^B$ is selected from the group consisting of hydrogen and $C_{1-6}$alkyl;

wherein the A ring portion of the ring structure is optionally substituted with one or more substituents independently selected from the group consisting of halogen, $C_{1-6}$alkyl, $C_{1-6}$alkoxy and aryl$C_{1-3}$alkyl;

Preferably, the bicyclic ring

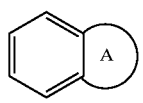

is selected from the group consisting of naphthyl, benzoxazolyl, benzothiazolyl, benzisoxazolyl, benzimidazolyl, quinolinyl, indolyl, benzothienyl, benzofuryl or a ring of the general structure

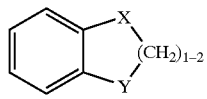

where X and Y are each independently selected from $CH_2$, O, S or NH.

In a preferred embodiment of the present invention, $R^2$ is selected from the group consisting of furyl, 3,4-methylenendioxyphenyl and 2,3-dihydrobenzofuryl. Preferably, $R^2$ is selected from the group consisting of 3,4-methylenendioxyphenyl and 2,3-dihydrobenzofuryl.

In an embodiment of the present invention $R^3$ is selected from the group consisting of hydrogen and $C_{1-4}$ alkyl. Preferably, $R^3$ is selected from the group consisting of hydrogen and methyl. Most preferably $R^3$ is hydrogen.

In an embodiment of the present invention m is an integer from 0 to 2. Preferably m is an integer from 0 to 1. In an embodiment of the present invention $R^4$ is selected from the group consisting of hydrogen and $C_{1-6}$alkyl.

Representative compounds of the present invention are listed in Tables 1–3.

TABLE 1

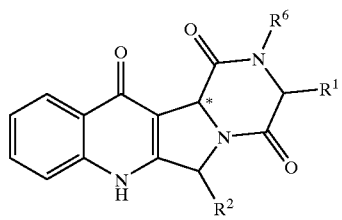

| ID No | Stereo (*) | $R^6$ | $R^2$ | $R^1$ |
|---|---|---|---|---|
| 1 | R | methyl | R-2,3-dihydrobenzofuryl | H |
| 2 | S | methyl | R-2,3-dihydrobenzofuryl | H |
| 3 | S | methyl | S-3,4-methylene dioxyphenyl | H |
| 4 | R | methyl | S-3,4-methylene dioxyphenyl | H |
| 5 | R | benzyl | R-3,4-methylene-dioxyphenyl | H |
| 8 | R | methyl | R-3,4-methylene-dioxyphenyl | H |
| 9 | S | methyl | R-3,4-methylene-dioxyphenyl | H |
| 10 | R | 2-pyridyl-methyl | R-2,3-dihydrobenzofuryl | H |
| 11 | R | methyl | 2-furyl | H |
| 12 | | 2-pyridyl-methyl | 2,3-dihydrobenzofuryl | methyl |
| 13 | | methyl | 2,3-dihydrobenzofuryl | methyl |

TABLE 2

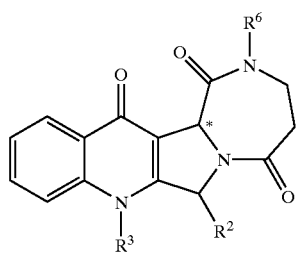

| ID No | Stereo (*) | $R^6$ | $R^2$ | $R^3$ |
|---|---|---|---|---|
| 7 | R | methyl | R-3,4-methylene-dioxyphenyl | H |

TABLE 3

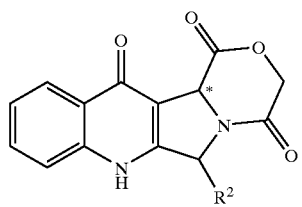

| ID No. | Stereo (*) | $R^2$ |
|---|---|---|
| 14 | — | 2,3-dihydrobenzofuryl |

The term "halogen" shall include iodine, bromine, chlorine and fluorine.

The term "alkyl", whether used alone or as part of a substituent group, shall mean straight or branched chain alkanes of one to ten carbon atoms, or any number within this range. For example, alkyl radicals include, methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl and 2-methylpentyl. Similarly, "alkenyl" and "alkynyl" groups include straight and branched chain alkenes and alkynes having two to ten carbon atoms, or any number within this range. Suitable alkenyl groups include, but are not limited to vinyl and allyl. Suitable examples of alkynyl groups include, but are not limited to acetylene The term "alkoxy" shall denote an oxygen ether radical of the above described straight or branched chain alkyl group. For example, alkoxy radicals include methoxy, ethoxy, n-propoxy, n-butoxy, sec-butoxy, tert-butoxy, and the like.

The term "halo$C_{1-6}$alkyl" shall mean an alkyl group as defined above substituted with one or more halogen atoms; for example trifluoromethyl, trichloromethyl, 2,2,2-trifluoroethyl, and the like. Similarly, the term "halo$C_{1-6}$alkyl" shall mean an alkoxy group as defined above substituted with one or more halogen atoms; for example trifluoromethoxy, trichloromethoxy, 2,2,2-trifluoroethoxy, and the like.

The term "aryl" indicates an aromatic group such as phenyl, naphthyl, and the like.

The term "aralkyl" denotes an alkyl group substituted with an aryl group. For example, benzyl, phenylethyl, and the like. Similarly, the term "aralkenyl" denotes an alkenyl group substituted with an aryl group, for example phenylethylenyl, and the like.

The term "heteroaryl" as used herein represents a stable five or six membered monocyclic aromatic ring system containing one to three heteroatoms independently selected from N, O or S; and any nine or ten membered bicyclic aromatic ring system containing carbon atoms and one to four heteroatoms independently selected from N, O or S. The heteroaryl group may be attached at any heteroatom or carbon atom which results in the creation of a stable structure. Examples of heteroaryl groups include, but are not limited to pyridyl, pyrimidinyl, thienyl, furyl, imidazolyl, isoxazolyl, oxazolyl, pyrazolyl, pyrazinyl, pyrrolyl, thiazolyl, thiadiazolyl, triazolyl, benzimidazolyl, benzofuranyl, benzothienyl, benzisoxazolyl, benzoxazolyl, indazolyl, indolyl, benzothiazolyl, benzothiadiazolyl, benzotriazolyl, quinolinyl, isoquinolinyl, purinyl.

The term "heterocycloalkyl" represents a stable saturated or partially unsaturated, three to eight membered monocyclic ring structure containing carbon atoms and one to four, preferably one to two, heteroatoms independently selected from N, O or S; and any stable saturated, partially unsaturated or partially aromatic, nine to ten membered bicyclic ring system containing carbon atoms and one to four heteroatoms independently selected from N, O or S. The heterocycloalkyl may be attached at any carbon atom or heteroatom which results in the creation of a stable structure. Suitable examples of heterocycloalkyl groups include pyrrolidinyl, pyrazolidinyl, piperidinyl, piperazinyl, morpholinyl, dithianyl, trithianyl, dioxolanyl, dioxanyl, thiomorpholinyl, 3,4-methylenedioxyphenyl, 2,3-dihydrobenzofuryl, 2,3-dihydrobenzo-[1,4]-dioxin-6-yl, 2,3-dihydro-furo[2,3-b]pyridyl, 1,2-(methylenedioxy) cyclohexane, indanyl, 2-oxa-bicyclo[2.2.1]heptanyl, and the like. Preferred heterocycloalkyl groups include 3,4-methylenedioxyphenyl, 2,3-dihydrobenzofuryl and 2,3-dihydrobenzo-[1,4]-dioxin-6-yl.

The term "cycloalkyl" as used herein represents a stable three to eight membered monocyclic ring structure consisting of saturated carbon atoms. Suitable examples include cyclopropyl, cyclobutyl, cyclopentyl, cyclohexyl, cycloheptyl and cyclooctyl.

As used herein, the notation "*" shall denote the presence of a stereogenic center.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. It is further intended that when m is >1, the corresponding $R^4$ substituents may be the same or different.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such intended to be included in the present invention. In addition, some of the compounds may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$–$C_6$ alkylaminocarbonyl$C_1$–$C_6$alkyl" substituent refers to a group of the formula

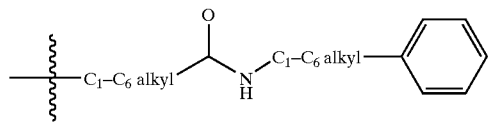

The term "sexual dysfunction" as used herein, includes male sexual dysfunction, male erectile dysfunction, impotence, female sexual dysfunction, female sexual arousal dysfunction and female sexual dysfunction related to blood flow and nitric oxide production in the tissues of the vagina and clitoris.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Abbreviations used in the specification, particularly the Schemes and Examples, are as follows:

| | |
|---|---|
| BOP = | Benzotriazol-1-yl-oxy-tris-dimethylamino)-phosphonium hexafluorophosphate (Castro's Reagent) |
| DIEA or DIPEA = | Diisopropylethylamine |
| DMF = | N,N'-Dimethylformamide |
| DMSO = | Dimethylsulfoxide |
| EDTA = | Ethylene diamine tetraacetic acid |
| HEPES = | 4-(2-Hydroxyethyl)-1-piperazine ethane sulfonic acid |
| KOt-Bu = | Potassium t-butoxide |
| PMSF = | Phenylmethylsulphonyl fluoride |
| PyBOP = | Benzotriazol-1-yl-oxy-tri-5-pyrrolidino-phosphonium hexafluorophosphate |
| PyBrOP = | Bromo-tris-pyrrolidino-phosphonium hexafluorophosphate |
| TEA = | Triethylamine |
| THF = | Tetrahydrofuran |
| TLC = | Thin Layer Chromatography |

Compounds of formula (I) wherein X is $NR^6$ may be prepared according to the process outlined in Scheme 1.

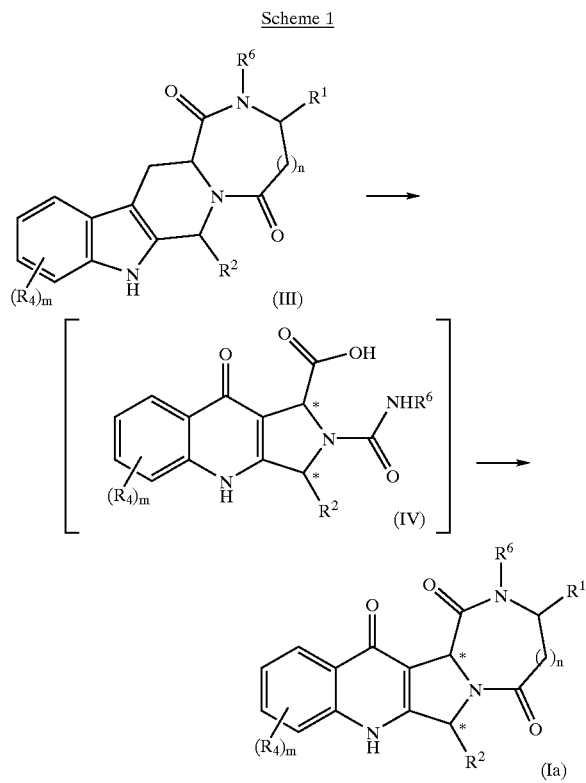

More particularly, a suitably substituted compound of formula (III); wherein n is 0 the compound of formula (III) is a known compound or compound prepared by known methods, (for example, according to the processes outlined in PCT publication WO 95/19978;) and wherein n is 1, the compound of formula (III) is prepared as in Scheme 4; is reacted with an oxidizing agent such as $NaIO_4$, $KO_2$, singlet oxygen, oxygen gas, ozone, dry air, and the like, preferably oxygen gas applied at about atmospheric pressure, to yield the corresponding compound of formula (IV). When the oxidizing agent is oxygen gas, the reaction is carried out in the presence of a base such as sodium hydride, potassium-t-butoxide, and the like.

The compound of formula (IV) is reacted with a coupling reagent such as PyBrOP, PyBOP, BOP, and the like, in the presence of an organic base such as DIPEA, TEA, pyridine, and the like, in an organic solvent such as DMF, methylene chloride, dioxane, DMSO, and the like, to yield the corresponding compound of formula (Ia).

Compounds of formula (I) wherein X is O may be prepared according to the process outlined in Scheme 2.

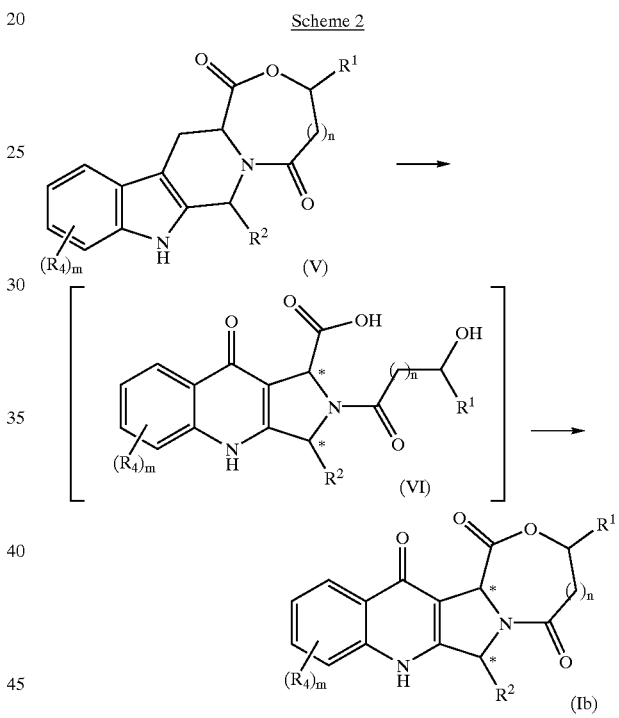

More particularly, a suitably substituted compound of formula (V); wherein n is 0, the compound of formula (V) is a known compound or compound prepared by known methods, (for example, according to the processes outlined in Malesic, M., Krbavcic, A and Stanovnik, B., J. Het. Chem., 1997, 34(1), pp. 49–55) and wherein n is 1, the compound of formula (V) may be prepared according to the process in Scheme 4; is reacted with an oxidizing agent such as $NaIO_4$, $KO_2$, singlet oxygen, oxygen gas, ozone, dry air, and the like, preferably oxygen gas applied at about atmospheric pressure, to yield the corresponding compound of formula (VI). When the oxidizing agent is oxygen gas, the reaction is carried out in the presence of a base such as sodium hydride, potassium-t-butoxide, and the like.

The compound of formula (VI) is reacted with a coupling reagent such as PyBrOP, PyBOP, BOP, and the like, in the presence of an organic base such as DIPEA, TEA, pyridine, and the like, in an organic solvent such as DMF, methylene chloride, dioxane, DMSO, and the like, to yield the corresponding compound of formula (Ib).

Compounds of formula (I) wherein $R^3$ is other than hydrogen and compounds of formula (II) may be prepared according to the process outlined in Scheme 3.

carried out in the presence of an organic or inorganic base such as triethylamine, diisopropylethylamine, potassium carbonate, sodium hydride, sodium hydroxide and the like.

Scheme 3

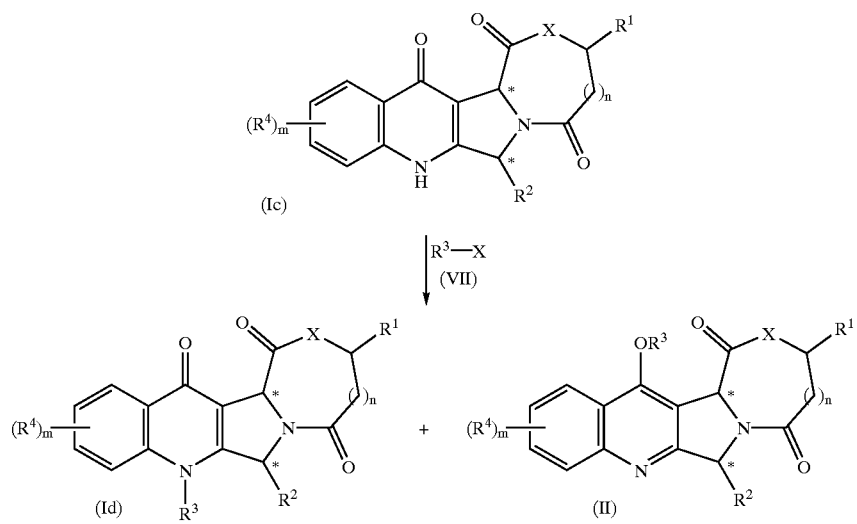

Accordingly, a suitably substituted compound of formula (Ic), a known compound or compound prepared as in Scheme 1 or 2 above, is reacted with a suitably substituted compound of formula (VI), wherein where X is halogen, hydroxy, tosylate, mesylate, and the like, preferably X is halogen, in an organic solvent such as THF, DMF, dichloromethane, toluene, and the like, preferably THF or DMF, to yield a mixture of the corresponding substituted The compounds of formula (Ie) and (II) are preferably separated by known methods such as recrystallization, column chromatography, HPLC, and the like.

Compounds of formula (III) and (V) wherein n is 1 may be prepared according to the process outlined in Scheme 4.

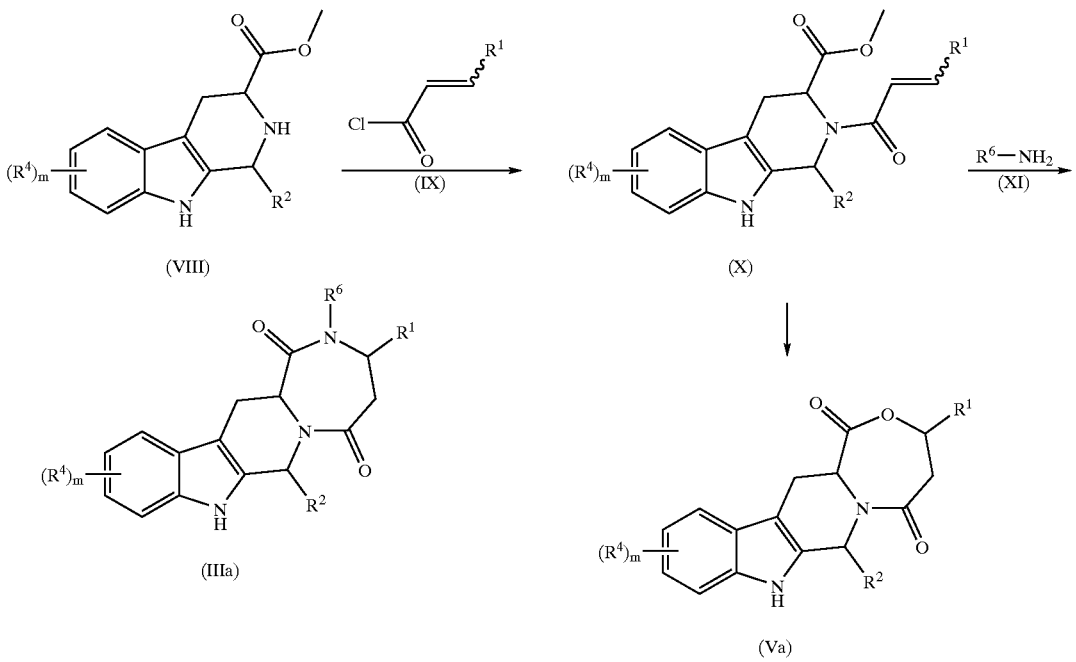

compound of formula (Id) and the corresponding substituted compound of formula (II). When in the compound of formula (VII), X is halogen, the reaction is preferably Accordingly, a suitably substituted compound of formula (VIII), a known compound or compound prepared by known methods is reacted with a suitably substituted compound of formula (IX), a known compound or compound prepared by known methods, in the presence of a base such as sodium carbonate, potassium carbonate, TEA, DIPEA, pyridine, and the like, in a non-protic solvent such as methylene chloride, dichloroethane, chloroform, THF and the like, at a reduced temperature in the range of about −10° C. to about room temperature to yield the corresponding compound of formula (X).

The compound of formula (X) is reacted with a suitably substituted compound of formula (XI), a known compound or compound prepared by known methods, in an organic solvent such as methanol, ethanol, and the like, at an elevated temperature in the range of about 0° C. to about 60° C., preferably a temperature in the range of about 40° C. to about 50° C., to yield the corresponding compound of formula (IIIa).

Alternatively, the compound of formula (X) is subjected to saponification, by reacting with a base such as sodium hydroxide, potassium hydroxide, and the like, in an aqueous solution, and followed by spontaneous cyclization to yield the corresponding compound of formula (Va).

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared by enantioselective synthesis, by resolution or from enantiomerically enriched reagents. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-I-tartaric acid followed by fractional crystallization and regeneration of the free base. The compounds may also be resolved by formation of diastereomeric esters, amides or amines, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The utility of the compounds to treat sexual dysfunction can be determined according to the procedures described in Examples 10 to 12 herein.

The present invention therefore provides a method of treating sexual dysfunction, more particularly male erectile dysfunction, in a subject in need thereof which comprises administering any of the compounds as defined herein in a quantity effective to treat ED. The compound may be administered to a patient by any conventional route of administration, including, but not limited to, intravenous, oral, subcutaneous, intramuscular, intradermal and parenteral. The quantity of the compound which is effective for treating ED is between 0.01 mg per kg and 20 mg per kg of subject body weight.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating sexual dysfunction, more particularly male erectile dysfunction described in the present invention may also be carried out using a pharmaceutical composition comprising any of the compounds as defined herein and a pharmaceutically acceptable carrier. The pharmaceutical composition may contain between about 1 mg and 1000 mg, preferably about 1 to 200 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of sexual dysfunction, more particularly male erectile dysfunction is required.

The daily dosage of the products may be varied over a wide range from 1 to 1,000 mg per adult human per day. For oral administration, the compositions are preferably provided in the form of tablets containing 1.0, 5.0, 10.0, 15.0, 25.0, 50.0, 100, 250 and 500 milligrams of the active ingredient for the symptomatic adjustment of the dosage to the patient to be treated. An effective amount of the drug is ordinarily supplied at a dosage level of from about 0.01 mg/kg to about 20 mg/kg of body weight per day. Preferably, the range is from about 0.1 mg/kg to about 10 mg/kg of body weight per day, and especially from about 0.1 mg/kg to about 3 mg/kg of body weight per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The following Examples are set forth to aid in the understanding of the invention, and are not intended and should not be construed to limit in any way the invention set forth in the claims which follow thereafter. Unless otherwise indicated, $^1$H NMRs were run on a Bruker instrument.

EXAMPLE 1

11-(2,3-Dihydro-benzofuran-5-yl)-3-methyl-2,3,4a, 11-tetrahydro-10H-3,10,11a-triaza-benzo[b]fluorene-1,4,5-trione; Compound # 1

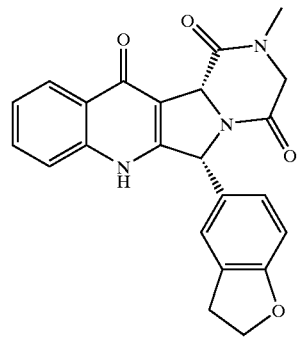

6-(2,3-Dihydro-benzofuran-5-yl)-2-methyl-2,3,6,7,12, 12a-hexahydro pyrazino[1',2':1,6]pyrido[3,4-b]indole-1,4-dione (39.6 mg, 0.1019 mmol), prepared according to Example 1 or 2 as described in WO97/03675, was dissolved in DMF (1.0 mL). To the solution was added KOt-Bu (0.173 mL, 1.0 M in THF). The solution was stirred under air (passed through drying tube) for 3 hours. Additional KOt-Bu (0.15 mL, 1.0 M in THF) was added and the reaction mixture stirred for another 3 hours under dry air. The reaction mixture was quenched by HCl (0.323 mL, 1.0 M HCl in ether) and the ether solvent evaporated. PyBrOP (53 mg, 0.1019 mmol) and DIPEA (0.036 mL, 0.204 mmol) were added, then DMF (0.2 mL) was added to make the total volume 1 mL. The resulting mixture was stirred at room temperature for 16 hours. Preparative TLC (1% CH$_3$OH/ CH$_2$Cl$_2$) yield the title product as a yellow solid.

$^1$H NMR 300 MHz (CD$_3$OD) δ3.05 (s, 3H), 3.15 (t, 2H, J=9.3 Hz), 3.54 (m, 1H), 4.05 (d, 1H, J=18 Hz), 4.28 (d, 1H, J=18 Hz), 4.57 (t, 2H, J=9.3 Hz), 4.72 (m, 1H), 6.65 (m, 1H), 6.92~7.32 (m, 5H), 7.51 (m, 1H), 7.98 (broad s, 1H; –NH) MS (m/z): 424 (MNa$^+$), 402 (MH$^+$), 825 (2MNa$^+$), 400 (MH$^-$)

Following the procedure described in Example 1, with appropriate selection and substitution of reagents, the following compounds of the instant invention were prepared.

EXAMPLE 2

11-(2,3-Dihydro-benzofuran-5-yl)-3-methyl-2,3,4a,
11-tetrahydro-10H-3,10,11a-triaza-benzo[b]fluorene-
1,4,5-trione; Compound # 2

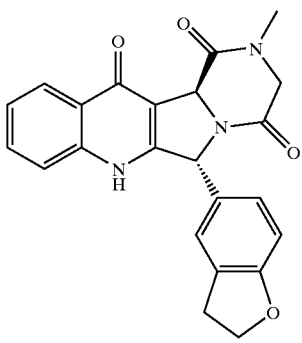

$^1$H NMR 300 MHz (CD$_3$OD) δ3.01~315 (m, 4H), 3.23 (s, 3H), 3.14 (t, 2H, J=9.3 Hz), 3.55 (m, 1H), 4.56 (t, 2H, J=9.3 Hz), 4.71 (m, 1H), 6.61 (m, 1H), 6.91~7.28 (m, 5H), 7.51 (m, 1H) MS (m/z): 424 (MNa$^+$), 402 (MH$^+$), 825 (2MNa$^+$), 400 (MH$^-$)

EXAMPLE 3

11-Benzo[1,3]dioxol-5-yl-3-methyl-2,3,4a,11-
tetrahydro-10H-3,10,11a-triaza-benzo[b]fluorene-1,
4,5-trione; Compound # 3

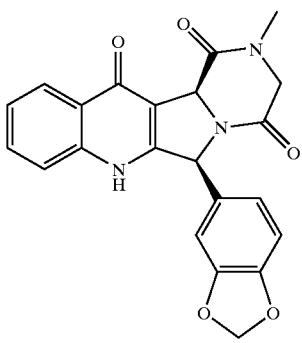

$^1$H NMR 300 MHz (CD$_3$OD) δ3.01~3.27 (m, 4H), 3.22 (s, 3H), 33.58 (m, 1H), 4.75 (m, 1H), 5.92 (m, 2H), 6.74~7.19 (m, 5H), 7.34 (d, 1H, J=10.34 Hz), 7.52 (d, 1H, J=10.34 Hz) MS (m/z): 426 (MNa$^+$), 404 (MH$^+$), 829 (2MNa$^+$), 402(MH$^-$)

EXAMPLE 4

11-Benzo[1,3]dioxol-5-yl-3-methyl-2,3,4a,11-
tetrahydro-10H-3,10,11a-triaza-benzo[b]fluorene-1,
4,5-trione; Compound # 4

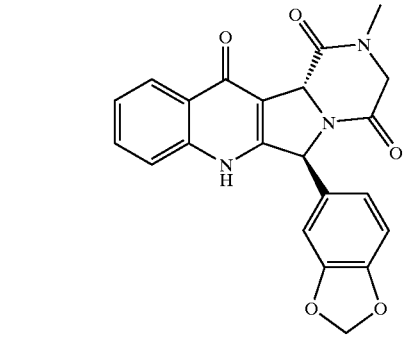

$^1$H NMR 300 MHz (CD$_3$OD) δ3.03 (s, 3H), 3.54 (m, 1H), 4.03 (m, 1H), 4.24 (m, 1H), 4.74 (m, 1H), 5.88 (m, 2H), 6.69~7.21 (m, 5H), 7.32 (d, 1H, J=10.75 Hz), 7.51 (d, 1H, J=10.75 Hz) MS (m/z): 426 (MNa$^+$), 404 (MH$^+$), 829 (2MNa$^+$), 402(MH$^-$)

EXAMPLE 5

11-Benzo[1,3]dioxol-5-yl-3-benzyl-2,3,4a,11-
tetrahydro-10H-3,10,11a-triaza-benzo[b]fluorene-1,
4,5-trione Compound # 5

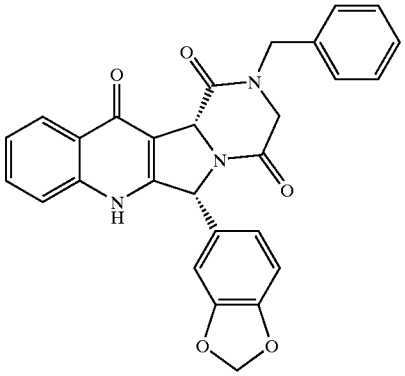

$^1$H NMR 300 MHz (CD$_3$OD) δ3.03 (m, 1H), 3.54 (m, 2H), 3.95 (m, 1H), 4.12 (m, 1H), 4.78 (m, 1H), 5.88 (m, 2H), 6.69~7.51 (m, 12H) MS (m/z): 502 (MNa$^+$), 981 (2MNa$^+$), 478 (MH$^-$)

EXAMPLE 6

11-Benzo[1,3]dioxol-5-yl-7-methyl-5b,8,9,12-tetrahydro-7H,11H-7,10a,12-triaza-naphtho[2,3-a]azulene-5,6,10-trione Compound # 7

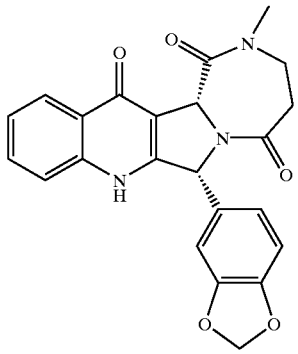

MS (m/z): 416 (MH+), 414 (MH−).

EXAMPLE 7

11-Benzo[1,3]dioxol-5-yl-3-methyl-2,3,4a,11-tetrahydro-10H-3,10,11a-triaza-benzo[b]fluorene-1,4,5-trione Compound # 8

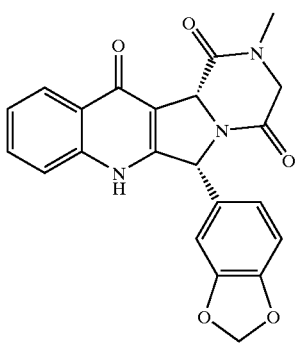

$^1$H NMR 300 MHz (CD$_3$OD) δ3.12 (m, 2H), 3.20 (s, 3H), 3.52 (m, 2H), 4.68 (m, 1H), 5.88 (m, 2H), 6.74 (s, 1H), 6.84 (s, 1H), 6.94 (s, 1H), 6.98~7.16 (m, 2H), 7.25 (d, 1H, J=10 Hz), 7.48 (d, 1H, J=10.0 Hz) MS (m/z): 404 (MH+), 426 (MNa+), 829 (2MNa+); 402 (MH−)

EXAMPLE 8

11-Benzo[1,3]dioxol-5-yl-3-methyl-2,3,4a,11-tetrahydro-10H-3,10,11a-triaza-benzo[b]fluorene-1,4,5-trione Compound # 9

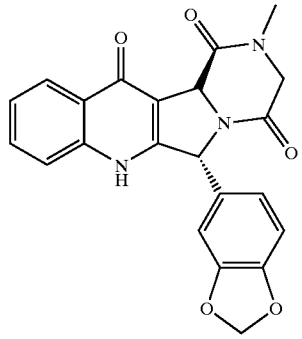

$^1$H NMR 300 MHz (CD$_3$OD) δ3.02 (s, 3H), 3.33 (m, 1H), 3.53 (m, 1H), 4.73 (m, 1H), 5.92 (m, b, 2H), 6.76 (s, 1H), 6.87 (s, 1H), 6.94 (s, 1H), 7.12 (m, 2H), 7.29 (d, 1H, J=8.7 Hz), 7.52 (d, 1H, J=8.7 Hz), 7.98 (s, 1H) MS (m/z): 404 (MH+), 426 (MNa+), 829 (2MNa+); 402 (MH−).

EXAMPLE 9

11-Benzo{1,3]dioxol-5-yl-3-pyridin-2-ylmethyl-2,3,4a,11-tetrahydro-10H-3,10,11a-triaza-benzo[b]fluorene-1,4,5-trione Compound # 10

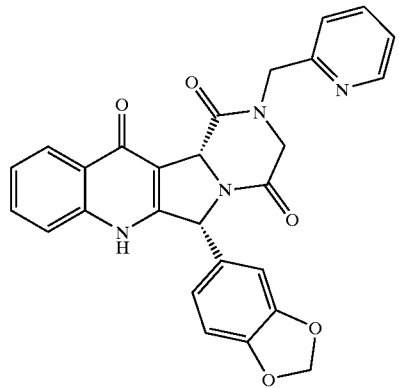

MS (m/z) 481 (MH+), 503 (MNa+), 983 (2MNa+), 479 (MH−)

EXAMPLE 10

In vitro Testing
Cyclic Nucleotide Phosphodiesterase (PDE) Assay
PDEV Isolation PDEV was isolated from rabbit and human tissues according to the protocol described by Boolell et al. (Boolell, M., Allen, M. J., Ballard, S. A., Ge[o-Attee, Muirhead, G. J., Naylor, A. M., Osterloh, I. H., and Gingell, C) in *International Journal of Impotence Research* 1996 8, 47–52 with minor modifications.

Briefly, rabbit or human tissues were homogenized in an ice-cold buffer solution containing 20 mM HEPES (pH 7.2), 0.25M sucrose, 1 mM EDTA, and 1 mM PMSF. The homogenates were centrifuged at 100,000 g for 60 minutes at 4° C. The supernatant was filtered through 0.2 µM filter and loaded on a Pharmacia Mono Q anion exchange column (1 ml bed volume) that was equilibrated with 20 mM HEPES, 1 mM EDTA and 0.5 mM PMSF. After washing out unbound proteins, the enzymes were eluted with a linear gradient of 100–600 mM NaCl in the same buffer (35 to 50 ml total, depending on the tissue. Enzymes from the skeletal muscle, corpus cavernosum, retina, heart and platelet were eluted with 35, 40, 45, 50, and 50 ml respectively.) The column was run at a flow rate of 1 ml/min and 1 ml fractions were collected. The fractions comprising various PDE activities were pooled separately and used in later studies.

Measurement of Inhibition of PDEV

The PDE assay was carried out as described by Thompson and Appleman in *Biochemistry* 1971 10, 311–316 with minor modifications, as noted below.

The assays were adapted to a 96-well format. The enzyme was assayed in 5 mM $MgCl_2$, 15 mM Tris HCl (pH 7.4), 0.5 mg/ml bovine serum albumin, 1 µM cGMP or cAMP, 0.1 µCi [$^3$H]-cGMP or [$^3$H]-cAMP, and 2–10 µl of column elution. The total volume of the assay was 100 µl. The reaction mixture was incubated at 30° C. for 30 minutes. The reaction was stopped by boiling for 1 minute and then cooled down on ice. The resulting [$^3$H]5'-mononucleotides were further converted to uncharged [$^3$H]-nucleosides by adding 25 µl 1 mg/ml snake venom (*Ophiophagus hannah*) and incubating at 30° C. for 10 minute. The reaction was stopped by the addition of 1 ml Bio-Rad AG1-X2 resin slurry (1:3). All the charged nucleotides were bound by the resin and only uncharged [$^3$H]-nucleosides remained in the supernatant after centrifuging. An aliquot of 200 µl was taken and counted by liquid scintillation. PDE activity was expressed as pmol cyclic nucleotide hydrolyzed/min/ml of enzyme preparation.

Inhibitor studies were carried out in assay buffer with a final concentration of 10% DMSO. Under these conditions, the hydrolysis of product increased with time and enzyme concentration in a linear fashion.

EXAMPLE 11

In Vitro Determination of $K_i$ for Phosphodiesterase Inhibitors

The assays were adapted to a 96-well format. Phosphodiesterase was assayed in 5 mM $MgCl_2$, 15 mM Tris HCl (pH 7.4), 0.5 mg/ml bovine serum albumin, 30 nM $^3$H-cGMP and test compound at various concentrations. The amount of enzyme used for each reaction was such that less than 15% of the initial substrate was converted during the assay period. For all measurements, the test compound was dissolved and diluted in 100% DMSO (2%DMSO in assay). The total volume of the assay was 100 µl. The reaction mixture was incubated at 30° C. for 90 minutes. The reaction was stopped by boiling for 1 minute and then immediately cooled by transfer to an ice bath. To each well was then added 25 µl 1 mg/ml snake venom (*Ophiophagus hannah*) and the reaction mixture incubating at 30° C. for 10 minute. The reaction was stopped by the addition of 1 ml Bio-Rad AG1-X2 resin slurry (1:3). An aliquot of 200 µl was taken and counted by liquid scintillation.

The % inhibition of the maximum substrate conversion (by the enzyme in the absence of inhibitor) was calculated for each test compound concentration. Using *GraphPad Prism's* nonlinear regression analysis (sigmoidal dose response), the % inhibition vs log of the test compound concentration was plotted to determine the $IC_{50}$. Under conditions where substrate concentration<<$K_m$ of the enzyme ($K_m$=substrate concentration at which half of the maximal velocity of the enzyme is achieved), $K_i$ is equivalent to the $IC_{50}$ value.

Following the procedures as described in Examples 10 and 11 herein, representative compounds of the instant invention were tested for PDEV and PDEVI activity. PDEV inhibitory activities for these compounds are presented as Ki values (nM) in the Table 4.

TABLE 4

| ID No | PDEV Ki (nM) |
| --- | --- |
| 1 | 7 |
| 2 | 69 |
| 3 | 17 |
| 4 | 80 |
| 5 | 123 |
| 7 | 148 |
| 8 | 14 |
| 9 | 48 |
| 10 | 63 |

EXAMPLE 12

In vivo Testing

Following the procedure disclosed by Carter et al., (Carter, A. J., Ballard, S. A., and Naylor, A. M.) in The Journal of Urology 1998, 160, 242–246, compound #8 was tested as active for in vivo activity.

EXAMPLE 13

As a specific embodiment of an oral composition, 100 mg of the compound of Example 1 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I) or (II):

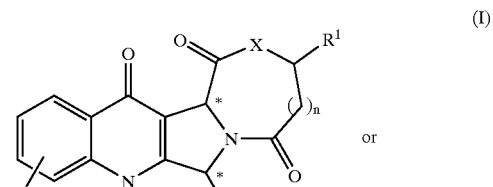

or

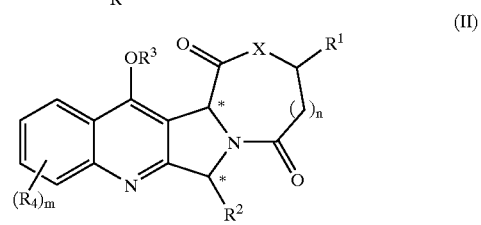

wherein
   X is selected from the group consisting of O and NR$^6$;
   R$^6$ is selected from the group consisting of hydrogen, C$_{1-6}$alkyl, C$_{2-6}$alkenyl, C$_{2-6}$alkynyl, haloC$_{1-6}$alkyl, C$_{3-8}$cycloalkyl, C$_{3-8}$cycloalkylC$_{1-3}$alkyl, arylC$_{1-3}$alkyl and heteroarylC$_{1-3}$alkyl;
   wherein the aryl part of the arylC$_{1-3}$alkyl group is phenyl or phenyl substituted with one or more substituents selected from halogen, C$_{1-6}$alkyl, C$_{1-6}$alkoxy and methylenedioxy; wherein the heteroaryl part of the heteroaiylC$_{1-3}$alkyl group is selected from thienyl, furyl or pyridyl wherein the thienyl, furyl or pyridyl group is optionally substituted with one or more substituents independently selected from halogen, C$_{1-6}$akyl or C$_{1-6}$alkoxy;
   R$^1$ is selected from the group consisting of hydrogen and C$_{1-3}$alkyl;
   alternatively R$^6$ and R$^1$ are taken together as C$_{3-4}$alkylene or C$_{3-4}$alkenylene;
   n is an integer from 0 to 1;
   R$^2$ is selected from the group consisting of C$_5$–C$_{10}$alkyl (optionally substituted with one to three substituents independently selected from halogen, hydroxy, nitro, amino, NHR$^A$ or N(R$^A$)$_2$), aryl (optionally substituted with one to three substituents independently selected from R$^C$), cycloalkyl (optionally substituted with one to three substituents independently selected from R$^A$), heteroaryl (optionally substituted with one to three substituents independently selected from R$^C$), and heterocycloalkyl (optionally substituted with one to three substituents independently selected from R$^C$);
   where each R$^A$ is independently selected from the group consisting of C$_1$–C$_6$alkyl, aryl, C$_1$–C$_6$aralkyl and heteroaryl, where the aryl, aralkyl or heteroaryl may be optionally substituted with one to three R$^B$;
   where each R$^B$ is independently selected from the group consisting of halogen, nitro, cyano, C$_1$–C$_6$alkyl, C$_1$–C$_6$alkoxy, C$_1$–C$_6$alkylcarbonyl, carboxyC$_1$–C$_6$alkyl, C$_1$–C$_6$alkylsulfonyl, trifluoromethyl, amino, di(C$_1$–C$_6$alkyl)amino, acetylamino, carboxyC$_1$–C$_6$alkylcarbonylamino, hydroxyC$_1$–C$_6$alkylamino, NHR$^A$ and N(R$^A$)$_2$;
   where R$^C$ is selected from the group consisting of halogen, hydroxy, nitro, cyano, —CO$_2$R$^D$, C$_1$–C$_6$alkyl, C$_1$–C$_6$alkoxy, trifluoromethyl, trifluoromethoxy, NR$^D$R$^E$ and arylC$_{1-3}$alkyl;
   where R$^D$ is selected from the group consisting of hydrogen and C$_{1-6}$alkyl; and where R$^E$ is selected from the group consisting of hydrogen, C$_{1-6}$alkyl, C$_{2-7}$alkylcarbonyl and C$_{1-6}$alkylsulfonyl;
   R$^3$ is selected from the group consisting of hydrogen, C$_{1-6}$alkyl, C$_1$–C$_6$alkylcarbonyl, C$_2$–C$_6$alkenylcarbonyl and C$_2$–C$_6$alkynylcarbonyl;
   m is and integer from 0 to 4;
      R$^4$ is independently selected from the group consisting of halogen, nitro, hydroxy, C$_1$–C$_6$alkyl, C$_1$–C$_6$alkoxy, —NH$_2$, —NHR$^A$, —N(R$^A$)$_2$, —OR$^A$, —C(O)NH$_2$, —C(O)NHR$^A$, —C(O)N(R$^A$)$_2$, —NHC(O)R$^A$, —SO$_2$NHR$^A$—SO$_2$N(R$^A$)$_2$, where R$^A$ is as defined above, phenyl (optionally substituted with one to three substituents independently selected from R$^B$), heteroaryl (optionally substituted with one to three substituents independently selected from R$^B$) and heterocycloalkyl (optionally substituted with one to three substituents independently selected from R$^B$);
   or a pharmaceutically acceptable salts thereof.

2. A compound as in claim 1 wherein
   R$^2$ is a monocyclic ring structure selected from phenyl, thienyl, furyl or pyridyl; or a bicyclic ring system of the general formula

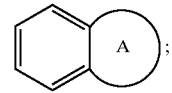

wherein the bicyclic ring structure is attached to the rest of the molecule via one of the benzene carbon atoms; wherein the fused ring A is a 5- or 6-membered saturated, partially unsaturated or fully unsaturated ring structure and which comprises carbon atom and optionally one to two heteroatoms selected from the group consisting of O, S and N;
   wherein the benzene portion of the ring structure is optionally substituted with one or more substituents independently selected from halogen, hydroxy, C$_{1-6}$alkyl, C$_{1-6}$alkoxy, —CO$_2$R$^B$, haloC$_{1-6}$alkyl, haloC$_{1-6}$alkoxy, cyano, nitro or NR$^A$R$^B$; where R$^A$ is selected from the group consisting of hydrogen, C$_{1-6}$alkyl, C$_{2-7}$alkylcarbonyl and C$_{1-6}$alkylsulfonyl; and where R$^B$ is selected from the group consisting of hydrogen and C$_{1-6}$alkyl;
   wherein the A ring portion of the ring structure is optionally substituted with one or more substituents independently selected from the group consisting of halogen, C$_{1-6}$alkyl, C$_{1-6}$ alkoxy and arylC$_{1-3}$alkyl;
   m is and integer from 0 to 2;
   R$^4$ is selected from the group consisting of halogen and C$_{1-6}$alkyl; and pharmaceutically acceptable salts thereof.

3. The compound of claim 2 wherein
   R$^6$ is selected from the group consisting of C$_{1-4}$alkyl, arylC$_{1-3}$alkyl and heteroarylC$_{1-3}$alkyl;
   R$^1$ is selected from the group consisting of hydrogen and C$_{1-3}$alkyl;
   R$^2$ is selected from furyl; or a bicyclic ring system of the general formula

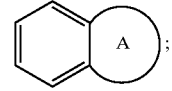

wherein the bicyclic ring structure is attached to the rest of the molecule via one of the benzene carbon atoms; wherein the fused A ring is a 5- or 6-membered fully unsaturated ring structure which comprises carbon atoms and optionally one to two O heteroatoms;
   R$^3$ is hydrogen;
   m is 0;
   and pharmaceutically acceptable salts thereof.

4. The compound of claim 3 wherein
   R$^6$ is selected from the group consisting of methyl, benzyl and 2-pyridylmethyl;
   R$^1$ is selected from the group consisting of hydrogen and methyl;
   R$^2$ is selected from the group consisting of 2,3-dihydrobenzofuryl, 3,4-methylenedioxyphenyl and furyl;
   and pharmaceutically acceptable salts thereof.

5. The compound of claim 4 wherein

X is $NR^6$;

$R^6$ is selected from the group consisting of methyl and 2-pyridylmethyl;

$R^1$ is hydrogen;

n is 0;

$R^2$ is selected from the group consisting of 2,3-dihydrobenzofuryl and 3,4-methylenedioxyphenyl;

and pharmaceutically acceptable salts thereof.

6. The compound of claim 4 wherein $R^6$ is methyl; and pharmaceutically acceptable salts thereof.

7. A pharmaceutical composition comprising a pharmaceutically acceptable carrier and a compound of claim 1.

8. A process for making a pharmaceutical composition comprising mixing a compound of claim 1 and a pharmaceutically acceptable carrier.

9. A method of treating sexual dysfunction in a subject in need thereof comprising administering to the subject a therapeutically effective amount of the compound of claim 1.

10. The method of treating sexual dysfunction of claim 9, wherein the sexual dysfunction is male sexual dysfunction, male erectile dysfunction, impotence, female sexual dysfunction, female sexual arousal dysfunction and female sexual dysfunction related to blood flow and nitric oxide production in the tissues of the vagina and clitoris.

11. A method for increasing the concentration of cGMP in penile tissue in a male subject comprising administering to the subject an effective amount of the compound of claim 1.

12. A method of treating a condition selected from the group consisting of male erectile dysfunction (ED), impotence, female sexual arousal dysfunction, female sexual dysfunction related to blood flow and nitric oxide production in the tissues of the vagina and clitoris, premature labor, dysmenorrhea, atherosclerosis, arterial occlusive disorders, thrombosis, coronary restenosis, angina pectoris, myocardial infarction, heart failure, ischemic heart disorders, hypertension, pulmonary hypertension, asthma, intermittent and claudication in a subject in need thereof comprising administering to the subject a therapeutically effective amount of the compound of claim 1.

* * * * *